United States Patent [19]

Lillard

[11] Patent Number: 5,141,435
[45] Date of Patent: Aug. 25, 1992

[54] ENDOSSEOUS DENTAL IMPLANT ASSEMBLY

[76] Inventor: Jonathan Lillard, 7311 Linganore Ct., McLean, Va. 22102

[21] Appl. No.: 503,904

[22] Filed: Apr. 4, 1990

[51] Int. Cl.⁵ .............................................. A61C 8/00
[52] U.S. Cl. ................................................. 433/176
[58] Field of Search ............ 433/173, 174, 176, 201.1

[56] References Cited

U.S. PATENT DOCUMENTS

| | | | |
|---|---|---|---|
| 2,258,207 | 10/1941 | Irwin | 433/173 |
| 2,449,522 | 9/1948 | White | 433/175 |
| 2,857,670 | 10/1958 | Kiernan, Jr. | 433/175 |
| 3,579,831 | 5/1971 | Stevens et al. | 433/174 |
| 3,738,008 | 6/1973 | Edelman | 433/176 |
| 4,439,152 | 3/1984 | Small | 433/174 |
| 4,622,010 | 11/1986 | Koch | 433/173 |
| 4,758,161 | 7/1988 | Niznick | 433/173 |
| 4,762,492 | 8/1988 | Nagai | 433/174 |
| 4,793,808 | 12/1988 | Kirsch | 433/173 |

FOREIGN PATENT DOCUMENTS 0317688 5/1989 European Pat. Off. ......... 433/201.1

*Primary Examiner*—Robert P. Swiatek
*Attorney, Agent, or Firm*—Roylance, Abrams, Berdo & Goodman

[57] ABSTRACT

A dental implant assembly for mounting a tooth replacement into a patient's jawbone, which includes a body member, a pair of wing or blade-shaped members movably coupled to the body member for movement from a retracted position to an extended position, and an implant head releasably coupled to the body member. The blade-shaped members have a cutting edge for cutting into the patient's jawbone to anchor the body member to resist both lateral and rotational movements caused by the patient chewing or grinding his or her teeth. The dental implant assembly may optionally include an extension member, a collar member, or both.

20 Claims, 3 Drawing Sheets

ENDOSSEOUS DENTAL IMPLANT ASSEMBLY

FIELD OF THE INVENTION

This invention relates to endosseous dental implant assemblies for mounting a tooth replacement to a patient's jawbone. More specifically, the invention relates to such dental implant assemblies having a body member and a detachable implant head.

BACKGROUND OF THE INVENTION

Oral implantology is a surgical technique which has come into rather wide use in recent years By this technique one or more implant devices are surgically and permanently affixed within or around the bone structure of a patient's jaw to serve as a support for the bridgework of artificial teeth. The implant device may be designed to have a portion set directly into the jawbone, i.e., an endosseous implant, or to be secured to the surface of the jawbone below the gum line, i.e., a subperiosteal implant. In either case, the implant device includes one or more projecting supports or posts which extend through the gum tissue to receive a prosthesis.

At the present time, there are various types of endosseous implants used in dentistry and oral surgery. The two most common types of endosseous implant devices are the cylindrical implant and the blade implant.

In the cylindrical implant, first a hole is drilled into the patient's jawbone, and then the cylindrical portion of the implant is inserted into the hole. The cylindrical implant is retained in the hole formed in the jawbone by pins, threads, etc. The cylindrical implant has a neck portion and an integral head portion which protrudes above the gum line for supporting and coupling an artificial tooth thereto.

The blade implant is implanted in a similar manner. First a groove is cut into the patient's jawbone, and then the implant is inserted into the groove in the patient's jawbone and secured in a conventional manner. The blade type also has an integral head which protrudes up above the gum line for attaching an artificial tooth thereto.

Over the years several studies have indicated that it is preferred that dental implants comprise detachable sections including an engaging section and a neck section so that initially, the engaging section of the implants can be completely retained within the jawbone and below the gum, until after the gum has healed and at least some bone material has grown about the engaging section. Accordingly, more recent dental implants are typically constructed of several pieces, i.e., including a detachable implant head.

A typical procedure for implanting a cylindrical dental implant device with a detachable implant head is disclosed in U.S. Pat. No. 4,439,152 to Small, which is incorporated by reference. In summary, first a hole is drilled into the patient's jawbone for receiving the cylindrical implant. Next, the implant device is inserted into the hole in the patient's jawbone, completely within the jawbone. The threaded hole at the top of the implant is closed with a removable plug. The gum is stitched closed and allowed to heal for two to three months. Subsequently, the patient's gum is reopened, the plug is removed and an implant head member is mounted on the implant. The implant head has a threaded shaft portion which screws into the bore of the implant cylinder for securing it thereto. Finally, a prosthesis or an artificial tooth is attached to the implant head.

Other examples of cylindrical implants with a threaded implant head are disclosed in U.S. Pat. Nos. 4,439,152 to Small and 4,793,808 to Kirsch. However, these cylindrical implants have numerous disadvantages. For example, these cylindrical implants have a tendency to become loose when rotational and/or lateral stresses or movements generated by chewing or grinding of the patient's teeth are applied thereto.

The blade implant was developed to resist rotational and lateral movements or stresses caused by the patient chewing or grinding his or her teeth. However, the blade implant also suffers from numerous disadvantages such as breaking. Another common problem with blade implants has been fibro-osseous integration, postulated by Charles Weiss Fibro-osseous integration occurs when a greater amount of fibrous tissue, i.e., a type of connective tissue, opposes the blade implant than the amount of bone tissue opposing the blade implant. Thus, there have been several attempts to combine a cylindrical implant and a blade implant Examples of such implant devices are disclosed in U.S. Pat. Nos. 2,449,522 to White; 4,622,010 to Koch; and 4,762,492 to Nagai. However, these implant devices require a large portion of the patent's jawbone to be removed for receiving the lower portion of the implant therein. Moreover, the implant devices are also difficult to implant in small areas between teeth.

Examples of implant devices which utilize pins for stabilizing the implant are disclosed in U.S. Pat. Nos. 2,857,670 to Kiernan, Jr. and 3,579,831 to Stevens et. al.

This invention addresses these problems in the art, along with other needs which will become apparent to those skilled in the art once given this disclosure.

SUMMARY OF THE INVENTION

Accordingly a primary object of the present invention is to provide an endosseous dental implant assembly that is firmly secured in the patient's jawbone for resisting rotational and lateral movements or stresses on the implant caused by the patient's chewing or grinding his or her teeth.

Another object of the present invention is to provide an endosseous dental implant that minimizes the amount of the patient's jawbone being removed for implanting the implant device into the patient's jawbone Another object of the present invention is to provide an endosseous dental implant assembly that prevents excess bone loss.

Yet another object of the present invention is to provide an endosseous dental implant that is compact for implanting into tight areas between teeth.

Still another object of the present invention is to provide an endosseous dental implant that has sufficient surface area for anchoring the implant in areas of minimal bone depth or height by expanding the blade members into the patient's jawbone and/or using the collar member. In particular, the blade members and collar member provides additional surface area for bone migration to occur for retaining the implant device in the patient's jawbone, which would otherwise be provided by a longer implant in areas of greater bone depth or height. In this way the dental implant assembly of the present invention may be implanted into areas of minimal bone depth or height, and thus avoid anatomical structures such as sinus cavities and inferior alveolar nerves.

Yet another object of the present invention is to provide an endosseous dental implant that has an upper extension member releasably coupled to the lower body member for replacing the extension member when natural bone loss has occurred, while the lower body member remains permanently affixed in the patient's jawbone.

Another object of the present invention is to provide an endosseous dental implant that has a large surface area for bone migration to reduce the number of implants utilized for supporting the artificial teeth.

The foregoing objects are basically attained by a dental implant assembly for mounting a tooth replacement to a patient's jawbone, the combination comprising: a body member having an upper end and an internal cavity, and which is adapted to be fitted within a tooth socket formed in the patient's jawbone; at least one blade member movably coupled to the body member, the blade member having a retracted position within the internal cavity and an extended position with the blade member extending out of the body member; and a first portion for coupling the tooth replacement to the upper end of the body member; whereby the blade member engages a portion of the patient's jawbone when the blade member is in the extended position and the implant assembly is in the tooth socket.

The foregoing objects are also basically attained by the method of mounting a tooth replacement to a patient's jawbone, comprising the steps of: forming a socket in a patient's jawbone for receiving a body member of a dental implant therein, the dental implant including at least one blade member having retracted and extended positions, inserting the body member into the socket with the blade member retracted, and moving the blade member to the extended position so that the blade member engages a portion of the patient's jawbone by cutting into the patient's jawbone.

In particular, the blade member cuts or engages the softer, internal portion of the patient's jawbone, i.e., the intermedullary or spongy bone portion, upon the blade member being moved outwardly to its extended position. Extension of the blade member may be accomplished by gently tapping the blade member outwardly, or by turning a threaded plug tool into the body member for engaging a portion of the blade member to move or force the blade member to its extended position.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring to the drawings which form part of this original disclosure.

DETAILED DESCRIPTION OF THE INVENTION

Figure 1:
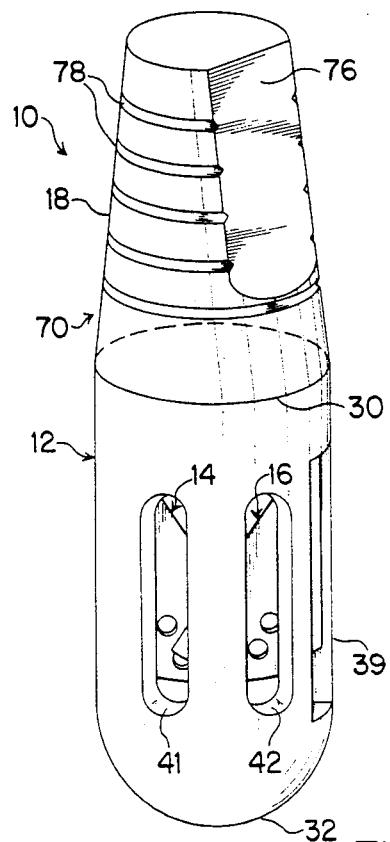
FIG. 1 is a front perspective view of a dental implant assembly in accordance with the present invention and having its blade-shaped members in their retracted positions.
Figure 2:
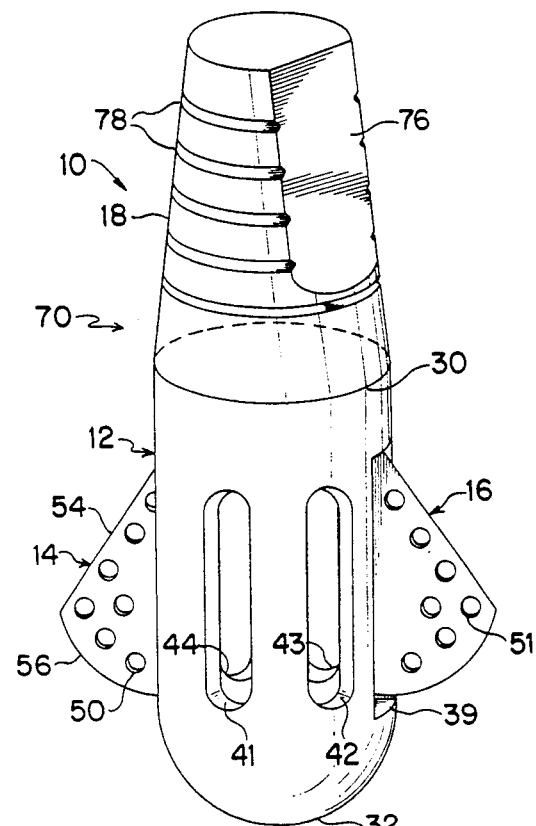
FIG. 2 is a front perspective view of the dental implant assembly of FIG. 1 with its blade-shaped members in their extended positions.

Referring initially to FIGS. 1 and 2, a dental implant assembly 10 in accordance with the present invention is illustrated and includes a body or base member 12, a pair of blade-shaped members 14 and 16 movably coupled to body member 12 for movement from a retracted position (FIG. 1) to an extended position (FIG. 2), and an implant head 18 releasably coupled to body member 12. Implant assembly 10 is adapted to be implanted into a patient's jawbone for mounting a tooth replacement thereon.

Figure 11:
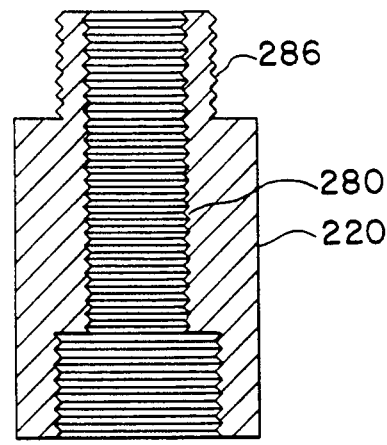
FIG. 11 is a front elevational view of a third embodiment of the extension member in cross section in accordance with the present invention.
Figure 12:
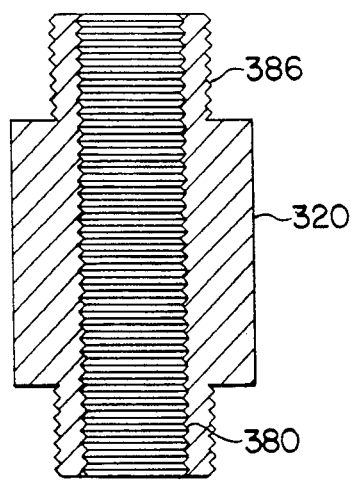
FIG. 12 is a fourth embodiment of the extension member in longitudinal cross section in accordance with the present invention.
Figure 13:
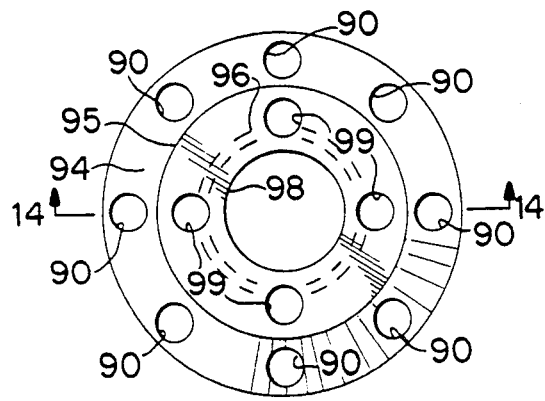
FIG. 13 is a top plan view of a collar member in accordance with the present invention.
Figure 14:
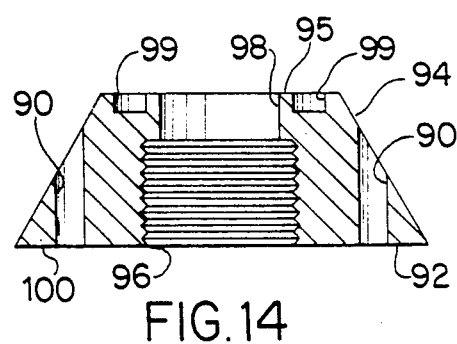
FIG. 14 is a front elevational view in cross section of the collar member taken along line 14—14 of FIG. 13.
Figure 15:
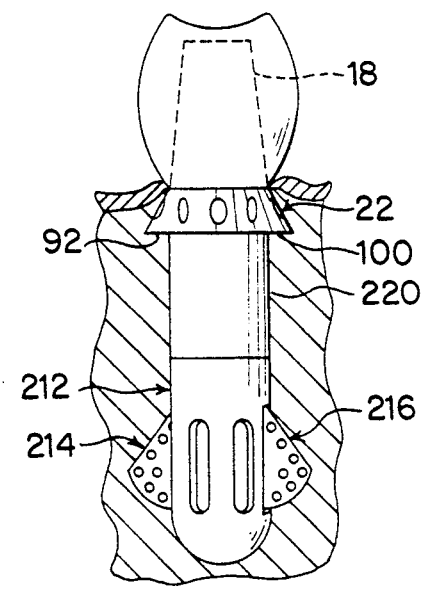
FIG. 15 is a front elevation view of a dental implant assembly in accordance with the present invention which has been implanted into the jawbone of a patient and has an extension member and a collar member coupled between the body member and the implant head.

Implant assembly 10 may optionally include an extension member 20, 120, 220 or 320 of various lengths as illustrated in FIGS. 8-12, a collar member 22, as illustrated in FIGS. 13-14, or both an extension member and collar member as illustrated in FIG. 15.

Body member 12 is substantially cylindrical and has a diameter preferably ranging from about 3.5 to about 4.0 millimeters and a length preferably ranging from about 8.0 to about 16.0 millimeters. The upper end 30 of body member 12 is substantially flat, while the lower end 32 is substantially semispherical. Preferably, body member 12 is made of surgical grade titanium having a rough outer surface, which can be achieved by knurling, sandblasting, or by plasma coating with titanium or hydroxyapatite.

Figure 3:
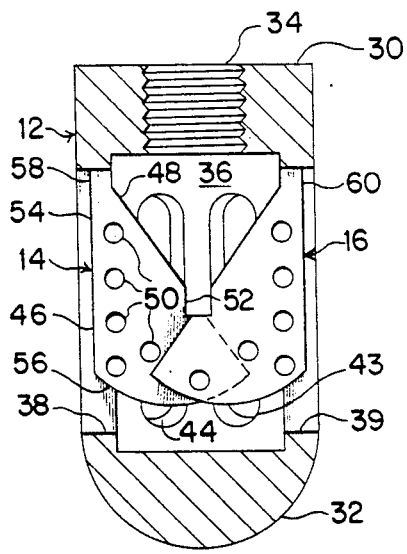
FIG. 3 is a front elevational view in cross section of the body member of FIG. 1 with the implant head removed.
Figure 4:
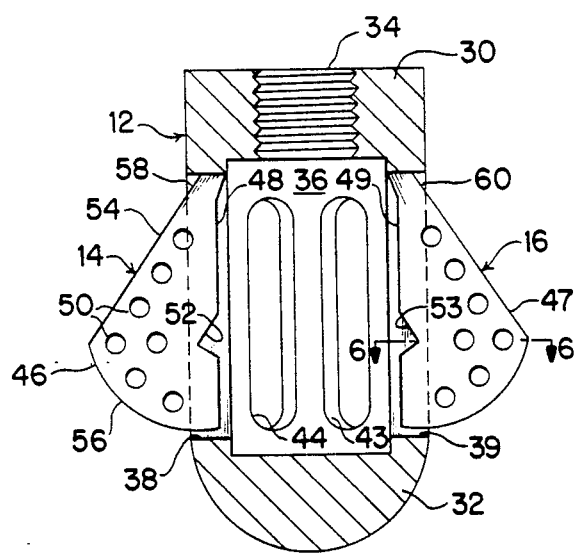
FIG. 4 is a front elevational view in cross section of FIG. 2 with the implant head removed and blade-shaped members extended.

As particularly seen in FIGS. 3 and 4, body member 12 also includes an axially extending threaded bore 34, internal cavity 36, blade slots 38 and 39, and openings 41, 42, 43 and 44. Threaded bore 34 extends from upper end 30 to internal cavity 36. Threaded bore 34 is approximately 2.0 millimeters in diameter and adapted to removably couple implant head 18 to body member 12. Threaded bore 34 permits access to internal cavity 36 for extending blade-shaped members 14 and 16 from their retracted positions to their extended positions, as discussed below.

Internal cavity 36 is substantially cylindrical and houses blade-shaped members 14 and 16 when they are in their retracted positions as seen in FIG. 3.

Body member 12 has a pair of longitudinally extending blade slots 38 and 39 extending through the outer surface of body member 12 and communicating with internal cavity 36 for permitting blade-shaped members 14 and 16 to be moved from their retracted positions to their extended positions.

Four elongated openings 41-44 extend longitudinally along the outer surface of body member 12 and communicate with internal cavity 36 for permitting bone from the patient's jawbone to grow therein for securely anchoring implant assembly 10 to the patient's jawbone. It should be apparent to those skilled in the art that fewer, or more elongated openings, such as openings 41-44, could be utilized in the present invention. Moreover, it should be apparent that openings 41-44 could be replaced with indentations to strengthen the body member.

Blade-shaped or wing members 14 and 16 are preferably made of surgical grade titanium. Blade-shaped members 14 and 16 preferably ranges in length from about 4.0 to about 14.0 millimeters along their inner surfaces 48 and 49, and ranges in width from about 3.0 to about 4.0 millimeters at their widest point depending upon application.

Blade-shaped member 14 includes a cutting edge 46, an inner surface 48, a plurality of bone growth holes 50 and a tool notch 52 formed in inner surface 48. Blade-shaped member 16 includes a cutting edge 47, an inner surface 49, a plurality of bone growth holes 51 and a tool notch 53 formed in inner surface 49. Each of the blade-shaped members 14 and 16 is substantially identical in shape, except they are oriented in opposite directions.

Cutting edge 46 of blade-shaped member 14 includes a substantially straight portion 54 and a curved portion 56, which are sufficiently sharp to cut into the patient's jawbone blade-shaped member 14 is moved from its retracted positions to its extended positions. Blade-shaped member 16 also includes the same portions.

Figures 5, 6:
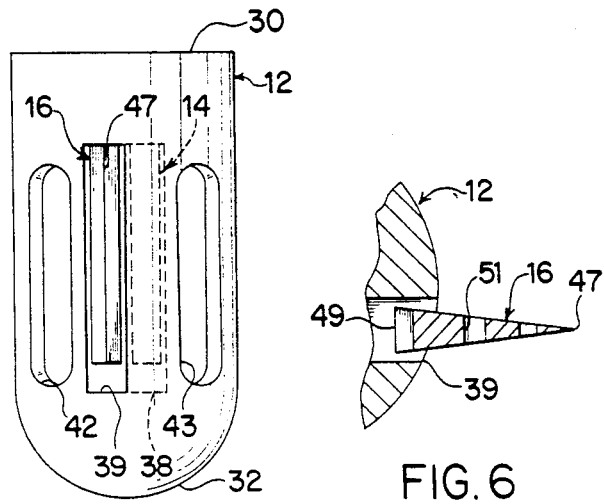
FIG. 5 is a side elevational view of the body member of FIG. 1 with the implant head removed and blade-shaped members retracted.
FIG. 6 is an enlarged, partial top view in cross section of the body member and one of the blade-shaped members taken along line 6—6 of FIG. 4.

As seen in FIG. 6, blade-shaped member 16 has a substantially wedge shaped cross section with a thickness of about 0.84 millimeters at its inner surface 49 and tapering to its sharp cutting edge 47. Of course, blade-shaped member 14 is also substantially wedge shaped.

While blade-shaped members 14 and 16 are each illustrated in elevation as substantially triangular shaped blades with seven bone growth holes 50 and 51, respectively, it will be apparent to those skilled in the art that other blade shapes with fewer or more holes of various shapes and sizes may be provided For example, each blade-shaped members 14 and 16 can be square, rectangular, semicircular, or any other suitable shape. If the blade-shaped members are substantially rectangular shaped blades, then the blade-shaped members should be oriented substantially vertically when in their retracted positions and oriented substantially horizontally when in their extended positions.

Tool notches 52 and 53 are positioned directly below threaded bore 34 of body member 12 when members 14 and 16 are in their retracted positions to permit an impact tool or a threaded plug to pass through threaded bore 34 and engage tool notches 52 and 53, for moving blade-shaped members 14 and 16 to their extended positions. If an impact tool is used, then the impact tool is gently tapped with a mallet to extend blade-shaped members 14 and 16.

On the other hand, if a threaded plug is used, then tool notches 52 and 53 may be eliminated and the threaded plug would be screwed into threaded bore 34 for engaging and extending blade-shaped members 14 and 16 outwardly. The threaded plug preferably has a conical point for engaging and moving blade-shaped members 14 and 16 outwardly. The threaded plug may be made of nylon, plastic or any other suitable material.

As seen in FIGS. 2 and 4, blade-shaped members 14 and 16 move substantially radially outwardly from body member 12 when moved from their retracted positions to their extended positions. Also blade-shaped members 14 and 16, as illustrated in FIGS. 3 and 5, overlap each other in their retracted positions to maximize the width of blade-shaped members 14 and 16. Of course, blade-shaped members 14 and 16 could be aligned with each other if they are smaller.

As seen in FIGS. 1-6, blade-shaped members 14 and 16 in the first embodiment are movably coupled to body members 12 by a pair of deformable flanges 58 and 60, respectively. Accordingly, portions 58 and 60 provide pivotal movement of blade-shaped members 14 and 16 from their retracted positions to their extended positions.

Figure 7:
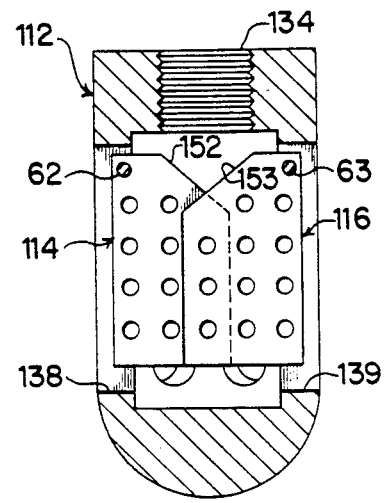
FIG. 7 is a front elevational view in cross section of a second embodiment of the body member utilizing pivot pins for movably coupling substantially rectangular blade-shaped members to the body member.

As seen in FIG. 7, a second embodiment of the body member is illustrated including body member 112, blade-shaped members 114 and 116 and pivot pins 62 and 63. Pivot pins 62 and 63 replace deformable flanges 58 and 60 for movably coupling blade-shaped members 114 and 116 to body member to 112. Body member 112 and blade-shaped members 114 and 116 are substantially identical to the first embodiment except for the overall shape of the blade-shaped members. Accordingly, body member 112 and blade-shaped members 114 and 116 will not be discussed in detail.

Blade-shaped members 114 and 116 are substantially rectangular shaped in elevation and substantially wedge shaped in transverse cross section. Blade-shaped member 114 and 116 are substantially identical and are movably coupled to body member 112 from substantially vertical positions when retracted to substantially horizontal positions when extended.

Tool engaging surfaces 152 and 153 of blade-shaped members 114 and 116 are provided beneath threaded bore 134 for moving blade-shaped members 114 and 116 to their extended positions.

It will also be apparent to those skilled in the art that blade-shaped members 14 and 16 or 114 and 116 may be movably coupled to body members 12 and 112, respectively, in any other suitable manner.

Implant head 18 includes a substantially frustoconical head portion 70 and a threaded shaft portion 72. Head portion 70 includes planar bottom surface 74, flat portion 76 and a plurality of grooves or score lines 78.

Flat portion 76 prevents rotation between the tooth replacement and head portion 70. Grooves or score lines 78 are spaced about one millimeter apart to aid in adjusting the height of head portion 70. Head portion 70 of implant head 18 is described in more detail by U.S. Pat. No. 4,758,161 to Niznick, which is incorporated herein by reference. Threaded shaft portion 72 extends axially from bottom surface 74 and is sized to be screwed into threaded bore 34 or 134 of body member 12 or 112, respectively, for releasably coupling implant head 18 thereto.

Figures 8, 9:
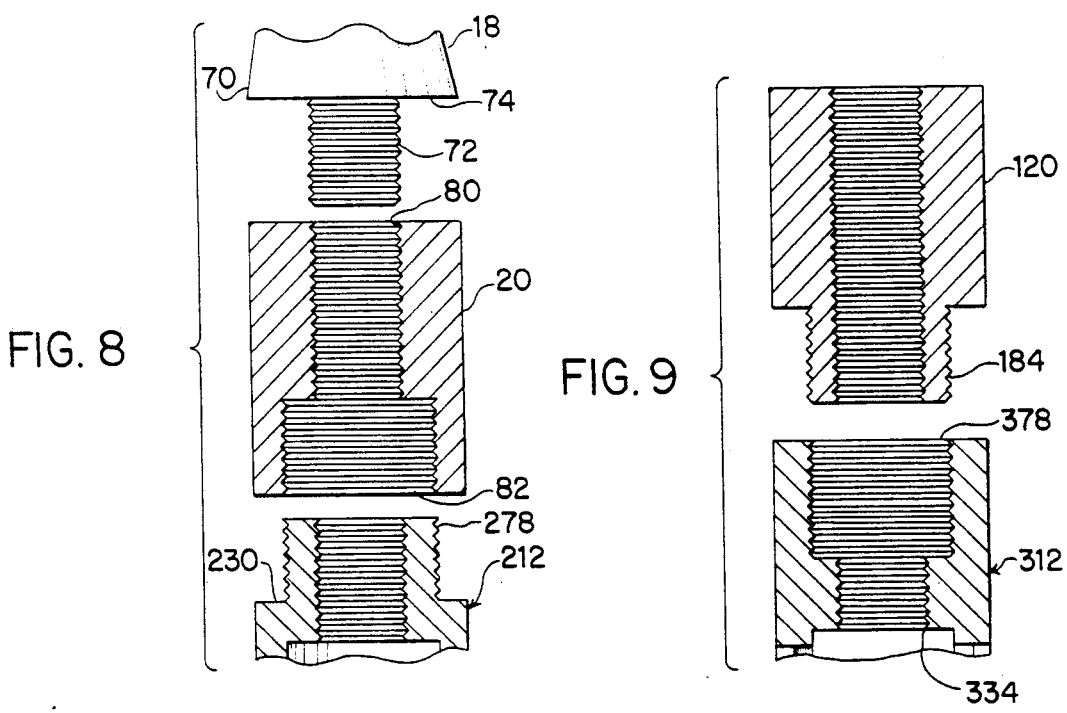
FIG. 8 is an exploded, front elevational view of a third embodiment of the body member in partial cross section in accordance with the present invention, an extension member in longitudinal cross section and an implant head in partial elevation.
FIG. 9 is an exploded, front elevational view of a fourth embodiment of the body member in partial cross section in accordance with the present invention and a second embodiment of the extension member shown in cross section.

As illustrated in FIG. 8, implant assembly 10 may also include an extension collar 20, which is releasably coupled between implant head 18 and a modified body member 212. Body member 212 is substantially identical to body member 12, except for the addition of an externally threaded shaft portion 278 extending axially from the upper end 230 of body member 212.

Extension member 20 is substantially cylindrical with its outer diameter substantially equal to the outer diameter of body member 212. Member 20 includes first axially extending threaded bore 80 to receive shaft portion 72 of implant head 18, and a second axially extending threaded bore 82, coaxial with first threaded bore 80, for threadedly receiving threaded shaft 278 of body member 212. Extension member 20 ranges in height from about 2.0 to about 10 millimeters depending upon the length needed. Extension member 20 is preferably made out of titanium and may be roughened in a similar manner as body member 12 as discussed above.

Bone loss often occurs in older people, who suffer from medical problems or conditions, such as diabetes or osteoporosis. Extension member 20 is particularly useful in these cases, when the bone loss has occurred around the upper portion of implant assembly 10, since extension member 20 may be removed while leaving body member 12 permanently fixed to the patient's jawbone. Accordingly, extension member 20 is simply unscrewed from body member 12, and a new sterile extension member 20, free of bacterial contamination is screwed to body member 12. Thus, the new extension member allows the bone to regrow about the new extension member without having to replace the entire implant device.

Referring now to FIG. 9, a modified extension member 120 and modified body member 312 are illustrated. Extension member 120 and body member 312 are substantially identical to extension member 20 and body member 12, as discussed above, except for the manner in which extension member 120 and body member 312 are coupled together. Thus, extension member 120 and body member 312 will not be discussed in detail.

Extension member 120 and body member 312 differ from extension member 20 and body member 12 as follows. Second internally threaded bore 82 of extension member 20 is replaced with an externally threaded shaft 184, in extension member 120. A second threaded bore 378 is provided in the upper-end of body member 312. Shaft 184 is threadedly received in threaded bore 378 of body member 312. Threaded bore 378 is located coaxially with threaded bore 334, which receives threaded-shaft 72 of implant head 18 when extension member 120 is not used. Accordingly, body member 312 may be used with or without extension member 120.

Referring now to FIGS. 11 and 12, further modified extension members 220 and 320 are illustrated, which are releasably coupled to modified member 212 and modified body member 312, respectively. In particular, extension member 220 is substantially identical to extension member 20, except for the addition of an externally threaded shaft 286 for releasably coupling collar member 22 (discussed below) thereto. Modified extension member 320, on the other hand, is substantially identical to modified extension member 120, except for the addition of an externally threaded shaft 386 for releasably coupling optional collar member 22 thereto. Accordingly, extension members 220 and 320 will not be discussed in detail.

Collar member 22 is substantially frustoconical and preferably made of surgical grade titanium or any other suitable material. Collar member 22 is particularly useful in increasing the anchoring of the implant assembly to the patient's jawbone. Accordingly, collar member 22 can be used in areas of minimal bone depth for increasing the surface area of the implant assembly to allow additional bone growth to anchor the implant to the patient's jawbone.

Collar member 22 includes a plurality of longitudinally extending bone growth bores 90, lower planar surface 92, inclined surface 94, upper planar surface 95, threaded bore 96, coaxially extending bore 98 and four tool receiving bores 99. Bore 90 extends from lower planar surface 92 through inclined surface 94. Bore 96 threadedly receives a threaded shaft 286 or 386 of extension member 220 or 320, respectively. Bore 98 is sized slightly larger than threaded shaft portion 72 of implant head 18 for permitting threaded shaft portion 72 to pass therethrough and threadedly engage internal threaded bore of 280 or 380 extension member 220 or 320, respectively. Tool receiving bores 99 are located in upper planar surface 95 for tightening collar member 22 with a special tool onto extension member 220 or 320.

Lower surface 92 of collar member 22 has a diameter which is approximately 3.0 to 4.0 millimeters larger than the diameter of the body member or the extension member being coupled thereto Accordingly lower surface 92 will protrude circumferentially outwardly from the body member or the extension member to form an annular ledge 100 approximately 1.5 to 2.0 millimeter wide. Ledge 100 exposes bores 90 to permit bone to migrate into bores 90 for firmly anchoring the implant assembly 10 and for added stability.

Implanting Procedure

Implant assembly 10 in accordance with the present invention is implanted into a patient's jawbone as follows. First, a socket or hole is formed in the patient's jawbone by drilling. Then body member 12, 112 or 212, with or without an extension member 20, 120, 220 or 320 and/or collar member 22 coupled thereto, is inserted into the socket with blade-shaped members in their retracted position. Next, blade-shaped members 14 and 16 are extended outwardly to their extended positions for fractionally engaging the jawbone of the patient. The blade-shaped members 14 and 16 may be extended by an impact tool or a threaded plug, as discussed above. If a threaded plug s used, it can be left in the body member 12, 112, or 212 to prevent bone growth in threaded bore 34. If an impact tool is used a nylon or other suitable material plug must be threaded into bore 34 to prevent bone growth therein. The patient's jawbone is then left to heal for two to three months to allow adjacent bone tissue to migrate into elongated openings 41-44 of body members 12, 112 or 212, holes 50 and 51 of blade-shaped members 14 and 16 or 114 and 116, and bores 90 if collar member 22 is used. The temporary plug is now removed by unthreading and implant head 18 having a dental prosthesis thereon is threaded into bore 34 of the body member or bore 80 of the extension member 20.

Figure 10:
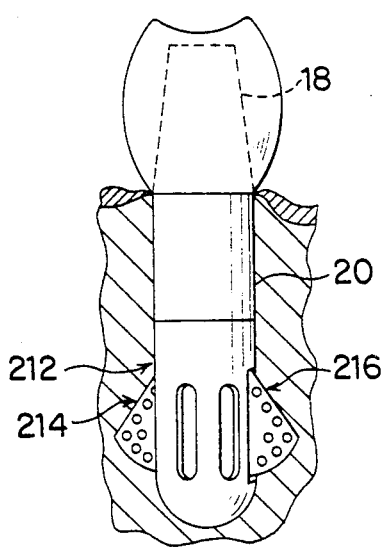
FIG. 10 is a front elevational view of a dental implant assembly in accordance with the present invention which has been implanted into the jawbone of a patient and has an extension member coupled thereto.

Referring now to FIG. 10, an implant assembly is illustrated in accordance with the present invention that has been implanted into a patient's jawbone pursuant to the described method, and utilizes body member 212 permanently fixed to the jawbone by blade-shaped members 214 and 216, and extension member 20 coupled between body member 212 and implant head 18.

While only selected embodiments have been chosen to illustrate the invention, it will be understood by those skilled in the art that various changes and modifications can be made herein without departing from the scope of the invention as defined in the appended claims.

What is claimed is:

1. A dental implant assembly for mounting a tooth replacement to a patient's jawbone, the combination comprising:
   a substantially tubular body member having an upper end and an internal cavity, and which is adapted to fit within a substantially tubular tooth socket formed in the patient's jawbone;
   at least one blade member having a pair of oppositely facing, substantially parallel side surfaces and movably coupled to said body member said at least one blade member having a retracted position within said internal cavity and an extended position wherein said at least one blade member extends out of said body member; and
   first means for coupling the tooth replacement to said upper end of said body member,
   whereby said at least one blade member engages a portion of the patient's jawbone when said at least one blade member is in said extended position and said implant assembly is in the tooth socket.

2. The dental implant assembly according to claim 1, wherein
   said at least one blade member is pivotally coupled to said body member.

3. The dental implant assembly according to claim 2, wherein
   said at least one blade member is pivotally coupled to said body member by a pivot pin between a substantially vertical position when retracted and a substantially horizontal position when extended.

4. The dental implant assembly according to claim 2, wherein
   said at least one blade member is movably coupled to said body member by a deformable portion extending between said at least one blade member and said body member.

5. The dental implant assembly according to claim 4, wherein
   said at least one blade member has an inner surface with a notch therein for receiving a tool.

6. The dental implant assembly according to claim 1, wherein
   said implant assembly includes two blade members.

7. The dental implant assembly according to claim 6, wherein
   said blade members are pivotally coupled to said body member and overlap when in their retracted positions.

8. The dental implant assembly according to claim 7, wherein
   said blade members are attached to said body member by pivot pins.

9. The dental implant assembly according to claim 8, wherein
   each of said blade members includes a notch adapted to receive a tool for pivoting said blade member to its extended position.

10. The dental implant assembly according to claim 7, wherein
    said blade members are movably attached to said body member by deformable portions extending between each of said blade members and said body member.

11. The dental implant assembly according to claim 10, wherein
    each of said blade members includes a notch adapted to receive a tool for pivoting said blade members to their extended positions.

12. The dental implant assembly according to claim 1, wherein
    said first means includes a threaded bore extending substantially longitudinally from said upper end of said body member to said internal cavity.

13. The dental implant assembly according to claim 12, further comprising
    an implant head having a threaded shaft adapted to be releasably coupled in said threaded bore.

14. The dental implant assembly according to claim 13, further comprising
    an extension member removably coupled between said implant head and said body member, and having a threaded bore adapted to threadedly receive said threaded shaft of said implant head therein.

15. The dental implant assembly according to claim 13, further comprising
    a frustoconical shaped collar member removably coupled between said implant head and said body member, and having a plurality of longitudinally extending bores.

16. The method of mounting a tooth replacement to a patient's jawbone, comprising the steps of:
    forming a substantially tubular socket in a patient's jawbone for receiving a substantially tubular body member of a dental implant therein, the dental implant including at least one blade member having a pair of oppositely facing, substantially parallel side surfaces and having retracted and extended positions,
    inserting the body member into the socket with the at least one blade member retracted into the body member, and
    moving the at least one blade member to the extended position protruding from the body member so that the at least one blade member engages a portion of the patient's jawbone.

17. The method of mounting a tooth replacement according to claim 16, wherein
    two blade members are expanded into a portion of the patient's jawbone.

18. A dental implant assembly for mounting a tooth replacement to a patient's jawbone, the combination comprising:
    a substantially tubular body member having an upper end and an internal cavity, and which is adapted to fit within a substantially tubular tooth socket formed in the patient's jawbone;

at least one blade member pivotably coupled to said body member between a substantially vertical, retracted position within said internal cavity and a substantially horizontal, extended position wherein said at least one blade member extends out of said body member; and first means for coupling the tooth replacement to said upper end of said body member, whereby said at least one blade member engages a portion of the patient's jawbone when said at least one blade member is in said extended position and said implant assembly is in the tooth socket.

19. The dental implant assembly according to claim 18, wherein
said implant assembly includes two blade members.

20. The dental implant assembly according to claim 19, wherein
said blade members overlap when in their retracted positions.

* * * * *